US009809477B2

(12) United States Patent
McHatton et al.

(10) Patent No.: US 9,809,477 B2
(45) Date of Patent: *Nov. 7, 2017

(54) PREVENTING AND REDUCING BIOFILM FORMATION AND PLANKTONIC PROLIFERATION

(71) Applicant: Novozymes Biologicials, Inc., Salem, VA (US)

(72) Inventors: Sarah McHatton, Salem, VA (US); Irene Michelle Williams, Roanoke, VA (US); David Drahos, Roanoke, VA (US)

(73) Assignee: NOVOZYMES BIOLOGICALS, INC., Salem, VA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/696,710

(22) Filed: Apr. 27, 2015

(65) Prior Publication Data

US 2015/0225272 A1  Aug. 13, 2015

Related U.S. Application Data

(63) Continuation of application No. 12/052,283, filed on Mar. 20, 2008, now abandoned.

(60) Provisional application No. 60/896,693, filed on Mar. 23, 2007.

(51) Int. Cl.
*C02F 3/34* (2006.01)
*A01N 63/00* (2006.01)

(52) U.S. Cl.
CPC ............ *C02F 3/341* (2013.01); *A01N 63/00* (2013.01); *C02F 3/34* (2013.01); *C02F 2303/04* (2013.01); *C02F 2303/20* (2013.01)

(58) Field of Classification Search
CPC ........ C02F 3/341; C02F 3/34; C02F 2303/04; C02F 2303/20; A01N 63/00
See application file for complete search history.

(56) References Cited

U.S. PATENT DOCUMENTS

| 4,655,794 A | 4/1987 | Richardson et al. |
| 5,171,591 A | 12/1992 | Whiting |
| 5,242,593 A | 9/1993 | Oberkofler |
| 5,360,517 A | 11/1994 | Guerineau et al. |
| 5,863,882 A | 1/1999 | Lin et al. |
| 6,140,106 A | 10/2000 | Lawler et al. |
| 6,376,451 B1 | 4/2002 | Teasdale |
| 6,743,361 B1 | 6/2004 | Doege et al. |
| 2002/0082184 A1 | 6/2002 | Teasdale et al. |
| 2003/0089381 A1 | 5/2003 | Manning, Jr. |
| 2004/0126365 A1 | 7/2004 | Villamar |

FOREIGN PATENT DOCUMENTS

| AU | 719544 | 3/1997 | |
| EP | 1010754 A1 | 6/2000 | |
| EP | 1283010 A1 * | 2/2003 | ............ A01N 63/00 |
| EP | 1719410 A1 | 11/2006 | |
| JP | 10-249388 | 9/1998 | |
| JP | 2001-299328 | 10/2001 | |
| JP | 2002-121593 | 4/2002 | |
| JP | 2002-226893 | 8/2002 | |
| JP | 2003-253299 | 9/2003 | |
| JP | 2005-232920 | 9/2005 | |
| JP | 2007-055982 | 8/2007 | |
| WO | 97/25865 A1 | 7/1997 | |
| WO | 98/39962 A1 | 9/1998 | |
| WO | 98/49104 A2 | 11/1998 | |
| WO | 00/63338 A1 | 10/2000 | |
| WO | 01/98214 A1 | 12/2001 | |
| WO | 03/002704 A1 | 1/2003 | |
| WO | 2006/031554 A2 | 3/2006 | |
| WO | 2006/125283 A1 | 11/2006 | |
| WO | 2008/021761 A2 | 2/2008 | |

OTHER PUBLICATIONS

English translation of EP1283010A1 (Penaud).Feb. 5, 2014. p. 1-9.*
Rai et al., Proceedings of the 6th WSEAS International Conference on Applied Informatics and Communications, pp. 474-480 (2006).

* cited by examiner

*Primary Examiner* — Taeyoon Kim
(74) *Attorney, Agent, or Firm* — Todd Sladek

(57) ABSTRACT

The present invention relates to methods for preventing and/or reducing biofilm formation and/or planktonic proliferation with one or more selected bacteria strains or bacterial blends.

13 Claims, 3 Drawing Sheets

PREVENTING AND REDUCING BIOFILM FORMATION AND PLANKTONIC PROLIFERATION

CROSS-REFERENCE TO RELATED APPLICATIONS

This application is a continuation of U.S. application Ser. No. 12/052,283 filed on Mar. 20, 2008, now abandoned, which claims priority or the benefit under 35 U.S.C. 119 of U.S. provisional application No. 60/896,693 filed Mar. 23, 2007. The content of each application is fully incorporated herein by reference.

FIELD OF THE INVENTION

The present invention provides methods and compositions for preventing and/or reducing biofilm formation on surfaces and/or planktonic proliferation in aqueous environments, especially in domestic/household and industrial settings.

BACKGROUND OF THE INVENTIONS

Biofilm formation and planktonic proliferation by undesired microorganisms are well known phenomena in domestic as well as industrial settings. For instance, toilet bowls harbor undesirable bacteria on surfaces and in solution that can contribute to a noticeably fouled appearance of the bowl. Further, the presence of undesired microorganisms in the bowl may cause dispersion of aerosols when flushing. Massive biofilm formation and planktonic proliferation in water systems, e.g., pipes, pumps and vessels, are known to cause health care risks, corrosion, and aesthetic problems.

Preventing or reducing biofilm formation and/or planktonic proliferation by undesirable microorganisms traditionally requires the use of dispersants, surfactants, enzymes, microbes, antimicrobial agents, biocides, boil-out procedures, and/or chemicals.

U.S. Pat. No. 5,171,591 concerns controlling or eliminating undesired bacteria in or on certain food or food contact surfaces using parasitic bacteria of the genus *Bdellovibrio*.

U.S. Pat. No. 5,242,593 concerns a method for reducing the buildup of slime and/or film in water circulation systems by adding non-sessile microbes in single form to the circulating water.

U.S. Pat. No. 5,360,517 discloses a process of regulating the growth of the microbial/bacterial flora existing in an aqueous papermaking circuit/process stream comprising introducing an effective disinfectant amount of bacteria of the species *Staphylococcus carnosus*.

U.S. Pat. No. 5,863,882 concerns liquid cleaning and sanitizing formulations comprising a sanitizing composition, viable *Bacillus* spores, and surfactants capable of reducing four pathogenic microorganisms.

AU Patent No. 719544 concerns a method of controlling the number of pathogenic bacteria in a body of water by adding non-pathogenic gram positive bacteria.

WO 2006/031554 disclose a method of preventing, removing, reducing or disrupting biofilms on surfaces by contacting said surface with an alpha-amylase derived from a bacterium.

Though methods of reducing and preventing biofilm formation and planktonic proliferation of undesired microorganisms are known in the art there is still a need for methods and compositions for doing so.

DESCRIPTION OF THE INVENTION

Figure 1:
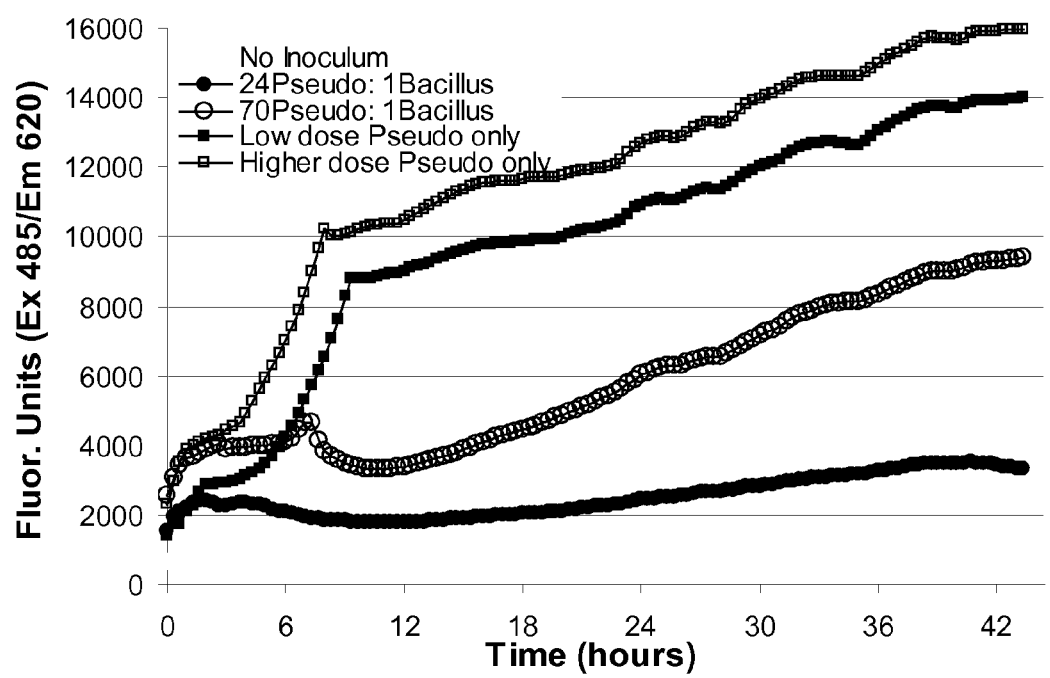
FIG. 1 shows reduced planktonic proliferation of *Pseudomonas* population in the presence of *Bacillus* blend (6BB) at different *Bacillus:Pseudomonas* ratios.

The present invention relates to methods and compositions for reducing and/or preventing biofilm formation and/or planktonic proliferation in aqueous environments.

The inventors have isolated and tested a significant number of bacteria strains for their ability to reduced and/or prevent biofilm formation and/or planktonic proliferation in aqueous environments. They found that a small number of the tested strains of the genus *Bacillus* can reduce and/or prevent biofilm formation and/or planktonic proliferation when co-cultured with undesirable microorganisms including *Pseudomonas aeruginosa*, *Pseudomonas montelli*, *Pseudomonas putida*, *Vibrio harveyi*, *Vibrio alginolyticus*, *Vibrio fischerii*, and/or *Escherichia coli*. This is described in detail in the Examples.

Methods for Preventing and/or Reducing Biofilm Formation

In the first aspect the invention relates to methods for preventing and/or reducing biofilm formation on a surface comprising subjecting said surface to one or more bacteria strains selected from the group consisting of:

the strain having the deposit accession number NRRL B-50014;
the strain having the deposit accession number NRRL B-50015;
the strain having the deposit accession number NRRL B-50016;
the strain having the deposit accession number NRRL B-50017;
the strain having the deposit accession number NRRL B-50018;
the strain having the deposit accession number PTA-7541;
the strain having the deposit accession number PTA-7542;
the strain having the deposit accession number PTA-7543;
the strain having the deposit accession number PTA-7544;
the strain having the deposit accession number PTA-7545;
the strain having the deposit accession number PTA-7546;
the strain having the deposit accession number PTA-7547;
the strain having the deposit accession number PTA-7549;
the strain having the deposit accession number PTA-7790;
the strain having the deposit accession number PTA-7791;
the strain having the deposit accession number PTA-7792;
the strain having the deposit accession number PTA-7793;
or a mixture of two or more of the strains.

In an embodiment the invention relates to methods for preventing and/or reducing biofilm formation on a surface comprising subjecting said surface to the strain having the deposit accession number NRRL B-50014. In an embodiment the invention relates to methods for preventing and/or reducing biofilm formation on a surface comprising subjecting said surface to the strain having the deposit accession number NRRL B-50015. In an embodiment the invention relates to methods for preventing and/or reducing biofilm formation on a surface comprising subjecting said surface to the strain having the deposit accession number NRRL B-50016. In an embodiment the invention relates to methods for preventing and/or reducing biofilm formation on a surface comprising subjecting said surface to the strain having the deposit accession number NRRL B-50017. In an embodiment the invention relates to methods for preventing and/or reducing biofilm formation on a surface comprising subjecting said surface to the strain having the deposit accession number NRRL B-50018. In an embodiment the invention relates to methods for preventing and/or reducing biofilm formation on a surface comprising subjecting said surface to the strain having the deposit accession number NRRL B-50019. In an embodiment the invention relates to methods for preventing and/or reducing biofilm formation on a surface comprising subjecting said surface to the strain having the deposit accession number PTA-7541. In an embodiment the invention relates to methods for preventing and/or reducing biofilm formation on a surface comprising subjecting said surface to the strain having the deposit accession number PTA-7542. In an embodiment the invention relates to methods for preventing and/or reducing biofilm formation on a surface comprising subjecting said surface to the strain having the deposit accession number PTA-7543. In an embodiment the invention relates to methods for preventing and/or reducing biofilm formation on a surface comprising subjecting said surface to the strain having the deposit accession number PTA-7544. In an embodiment the invention relates to methods for preventing and/or reducing biofilm formation on a surface comprising subjecting said surface to the strain having the deposit accession number PTA-7545. In an embodiment the invention relates to methods for preventing and/or reducing biofilm formation on a surface comprising subjecting said surface to the strain having the deposit accession number PTA-7546. In an embodiment the invention relates to methods for preventing and/or reducing biofilm formation on a surface comprising subjecting said surface to the strain having the deposit accession number PTA-7547. In an embodiment the invention relates to methods for preventing and/or reducing biofilm formation on a surface comprising subjecting said surface to the strain having the deposit accession number PTA-7549. In an embodiment the invention relates to methods for preventing and/or reducing biofilm formation on a surface comprising subjecting said surface to the strain having the deposit accession number PTA-7550. In an embodiment the invention relates to methods for preventing and/or reducing biofilm formation on a surface comprising subjecting said surface to the strain having the deposit accession number PTA-7789. In an embodiment the invention relates to methods for preventing and/or reducing biofilm formation on a surface comprising subjecting said surface to the strain having the deposit accession number PTA-7790. In an embodiment the invention relates to methods for preventing and/or reducing biofilm formation on a surface comprising subjecting said surface to the strain having the deposit accession number PTA-7791. In an embodiment the invention relates to methods for preventing and/or reducing biofilm formation on a surface comprising subjecting said surface to the strain having the deposit accession number PTA-7792. In an embodiment the invention relates to methods for preventing and/or reducing biofilm formation on a surface comprising subjecting said surface to the strain having the deposit accession number PTA-7793.

In an embodiment a blend of bacteria may be used according to the method of the invention. Examples of blends can be found below in the section "Bacteria strains and Blends of Bacteria strains".

The term "biofilm formation" means the formation of a slime layer or film by undesired microorganisms on a surface. Biofilm formation is a consequence of growth of undesired microorganisms which attach singly or in colonies to a surface.

The term "surface" refers to any surface, preferably hard surfaces, which may be prone to biofilm formation and adhesion of microorganisms. Examples of contemplated surfaces include hard surfaces made from one or more of the following materials: metal, plastic, rubber, board, glass, wood, paper, concrete, rock, marble, gypsum and ceramic materials, such as porcelain, which optionally are coated, for example, with paint or enamel. Examples of soft surfaces include surfaces made of fibers of any kind (e.g., yarns, textiles, vegetable fibers, rock wool, and hair); or any porous surface; skin (human or animal); keratinous materials (e.g., nails); and internal organs (e.g., lungs).

Hard surfaces are, for instance, found in bathrooms, e.g., fixtures, sinks, bathtubs, toilet bowls, and rinse water reservoirs; in cooling towers; water treatment plants; water tanks; dairy, food processing plants etc.; chemical or pharmaceutical process plants; or medical devices (e.g., catheters, orthopedic devices, and implants). Biofilm prone surfaces may also be porous surfaces. Porous surfaces can, for instance, be present in filters, e.g., membrane filters.

Methods for Preventing and/or Reducing Planktonic Proliferation

The invention also relates to methods for preventing and/or reducing planktonic proliferation of microorganism(s), comprising subjecting said microorganism(s) in aqueous solution to one or more bacteria strains selected from the group consisting of:
  the strain having the deposit accession number NRRL B-50014;
  the strain having the deposit accession number NRRL B-50015;
  the strain having the deposit accession number NRRL B-50016;
  the strain having the deposit accession number NRRL B-50017;
  the strain having the deposit accession number NRRL B-50018;
  the strain having the deposit accession number PTA-7541;
  the strain having the deposit accession number PTA-7542;
  the strain having the deposit accession number PTA-7543;
  the strain having the deposit accession number PTA-7544;
  the strain having the deposit accession number PTA-7545;
  the strain having the deposit accession number PTA-7546;
  the strain having the deposit accession number PTA-7547;
  the strain having the deposit accession number PTA-7549;
  the strain having the deposit accession number PTA-7790;
  the strain having the deposit accession number PTA-7791;
  the strain having the deposit accession number PTA-7792;
  the strain having the deposit accession number PTA-7793;
  or a mixture of two or more of the strains.

In an embodiment the invention relates to methods for preventing and/or reducing planktonic proliferation of microorganism(s), comprising subjecting said microorganism(s) in aqueous solution to the strain having the deposit accession number NRRL B-50014. In an embodiment the invention relates to methods for preventing and/or reducing planktonic proliferation of microorganism(s), comprising subjecting said microorganism(s) in aqueous solution to the strain having the deposit accession number NRRL B-50015. In an embodiment the invention relates to methods for preventing and/or reducing planktonic proliferation of microorganism(s), comprising subjecting said microorganism(s) in aqueous solution to the strain having the deposit accession number NRRL B-50016. In an embodiment the invention relates to methods for preventing and/or reducing planktonic proliferation of microorganism(s), comprising subjecting said microorganism(s) in aqueous solution to the strain having the deposit accession number NRRL B-50017. In an embodiment the invention relates to methods for preventing and/or reducing planktonic proliferation of microorganism(s), comprising subjecting said microorganism(s) in aqueous solution to the strain having the deposit accession number NRRL B-50018. In an embodiment the invention relates to methods for preventing and/or reducing planktonic proliferation of microorganism(s), comprising subjecting said microorganism(s) in aqueous solution to the strain having the deposit accession number NRRL B-50019.

In an embodiment the invention relates to methods for preventing and/or reducing planktonic proliferation of microorganism(s), comprising subjecting said microorganism(s) in aqueous solution to the strain having the deposit accession number PTA-7541. In an embodiment the invention relates to methods for preventing and/or reducing planktonic proliferation of microorganism(s), comprising subjecting said microorganism(s) in aqueous solution to the strain having the deposit accession number PTA-7542. In an embodiment the invention relates to methods for preventing and/or reducing planktonic proliferation of microorganism(s), comprising subjecting said microorganism(s) in aqueous solution to the strain having the deposit accession number PTA-7543. In an embodiment the invention relates to methods for preventing and/or reducing planktonic proliferation of microorganism(s), comprising subjecting said microorganism(s) in aqueous solution to the strain having the deposit accession number PTA-7544. In an embodiment the invention relates to methods for preventing and/or reducing planktonic proliferation of microorganism(s), comprising subjecting said microorganism(s) in aqueous s solution to the strain having the deposit accession number PTA-7545. In an embodiment the invention relates to methods for preventing and/or reducing planktonic proliferation of microorganism(s), comprising subjecting said microorganism(s) in aqueous solution to the strain having the deposit accession number PTA-7546. In an embodiment the invention relates to methods for preventing and/or reducing planktonic proliferation of microorganism(s), comprising subjecting said microorganism(s) in aqueous solution to the strain having the deposit accession number PTA-7547. In an embodiment the invention relates to methods for preventing and/or reducing planktonic proliferation of microorganism(s), comprising subjecting said microorganism(s) in aqueous solution to the strain having the deposit accession number PTA-7549. In an embodiment the invention relates to methods for preventing and/or reducing planktonic proliferation of microorganism(s), comprising subjecting said microorganism(s) in aqueous solution to the strain having the deposit accession number PTA-7550. In an embodiment the invention relates to methods for preventing and/or reducing planktonic proliferation of microorganism(s), comprising subjecting said microorganism(s) in aqueous solution to the strain having the deposit accession number PTA-7789. In an embodiment the invention relates to methods for preventing and/or reducing planktonic proliferation of microorganism(s), comprising subjecting said microorganism(s) in aqueous solution to the strain having the deposit accession number PTA-7790. In an embodiment the invention relates to methods for preventing and/or reducing planktonic proliferation of microorganism(s), comprising subjecting said microorganism(s) in aqueous solution to the strain having the deposit accession number PTA-7791. In an embodiment the invention relates to methods for preventing and/or reducing planktonic proliferation of microorganism(s), comprising subjecting said microorganism(s) in aqueous solution to the strain having the deposit accession number PTA-7792. In an embodiment the invention relates to methods for preventing and/or reducing planktonic proliferation of microorganism(s), comprising subjecting said microorganism(s) in aqueous solution to the strain having the deposit accession number PTA-7793.

In an embodiment a blend of bacteria may be used according to the method of the invention. Examples of blends can be found below in the section "Bacteria strains and Blends of Bacteria strains".

The term "planktonic proliferation" means growth of undesired microorganisms, preferably undesired bacteria, in an aqueous environment, such as a body of water. The undesired microorganisms typically occur freely in the aqueous environment. Examples of contemplated aqueous environments are rinse water in toilet bowls and cooling water circulated in plants.

Bacteria Strains and Blends of Bacteria Strains

It is to be understood that a bacteria strain used in accordance with methods of the invention may be a culture of one of the above mentioned deposited strains, but may also be a culture of a strain which has properties substantially identical to the above mentioned isolated and deposited strains. In a preferred embodiment the strain is one of the deposited strains or a progeny thereof.

The bacteria strain(s) may be (an) active ingredient(s) in compositions also comprising other active and/or inactive ingredients.

The terms "effective amount", "effective concentration" or "effective dosage" are defined herein as the amount, concentration or dosage of one or more bacteria strains that can reduce and/or prevent biofilm formation caused by undesired microorganisms on a surface and/or reduce and/or prevent planktonic proliferation of undesired microorganisms in an aqueous environment. The actual effective dosage in absolute numbers depends on factors including: the undesired microorganism(s) in question; whether the aim is prevention or reduction; the contact time between the strain(s) or composition comprising said strain(s); other ingredients present, and also the surface or aqueous environment in question. In an embodiment an effective dosage of bacteria, e.g., of the six strains Bacillus blends mentioned below, would be in the range from 1 to $1 \times 10^8$ cfu/ml, preferably 50 to $1 \times 10^7$ cfu/ml. Further, in an embodiment the ratio between the bacteria strain or blends concerned herein and the undesired microorganism(s) in question may be between 1:100,000 and 100,000:1 (strain/blend:undesired microorganism), preferably 1:10,000 to 10,000:1, more preferably 1:1,000 to 1,000:1, more preferably 1:100 to 100:1, even more preferably 1:10 to 10:1.

In general, environments that receive high loads of undesirable microorganisms and nutrients require high doses of mitigating bacteria strains, while environments with low loads of undesirable organisms require lower doses of mitigating bacteria strains. Further, for instance, preventing biofilm formation on surfaces or preventing planktonic formation in aqueous environments, in general, require lower doses of the concerned bacteria strain(s) than reducing biofilm formation on corresponding surfaces or reducing the number of already existing undesired microorganism(s) in corresponding aqueous environments.

Consequently, a method of the invention can be used for inhibiting growth (i.e., leading to reduced biofilm formation) of one or more undesired microorganisms, preferably bacteria already present on a surface or already present in an aqueous environment. In another embodiment the invention relates to preventing and/or significantly retarding biofilm formation on an essentially clean surface (i.e., surface with essentially no undesired microorganisms) and/or planktonic proliferation in essentially clean water (i.e., aqueous environment containing essentially no undesired microorganisms). In other words, the concerned bacteria strain(s) protect(s) the surface and/or aqueous environment against future growth of one or more undesired microorganisms. A method of the invention may result in reduction or even elimination/removal of already existing undesired microorganisms. The concerned bacteria strain(s) may in a preferred embodiment be applied to the surface in question and/or or added to the aqueous environment in question periodically. Periodically means that the method of the invention may be reiterated or repeated over a period of time, e.g., every minute, hour, day, week, month, etc. As mentioned above, the effect may not last for a long period of time. It may require redosing of bacteria strains. For instance, when the surface and aqueous environment is on the inside of a toilet bowl and the rinsing water in the toilet bowl, respectively, redosing may take place (periodically), e.g., with every flushing. The concerned bacteria strain(s) may, for instance, be incorporated into a rim block.

A method of the invention may also be carried out by manually and/or mechanically subjecting (i.e., applying or contacting) the bacteria strain(s) or composition comprising one or more bacteria strains (i.e., blends) to the surface in question.

In a preferred embodiment the bacteria, that may be used alone or in combination with other bacteria, is NRRL B-50014. In a preferred embodiment the bacteria, that may be used alone or in combination with other bacteria, is NRRL B-50015. In a preferred embodiment the bacteria, that may be used alone or in combination with other bacteria, is NRRL B-50016. In a preferred embodiment the bacteria, that may be used alone or in combination with other bacteria, is NRRL B-50017. In a preferred embodiment the bacteria, that may be used alone or in combination with other bacteria, is NRRL B-50018.

In a preferred embodiment the bacteria strains is a blend of two, three, four, five or six of the following deposited strains deposited on 14 Mar. 2007: NRRL B-50014, NRRL B-50015, NRRL B-50016, NRRL B-50017, NRRL B-50018, and NRRL B-50019.

In another preferred embodiment the bacteria strains is a blend of two, three, four, or five of the following deposited strains deposited on 14 Mar. 2007: NRRL B-50014, NRRL B-50015, NRRL B-50016, NRRL B-50017, and NRRL B-50018. It should be understood that a blend of the invention may or may not comprise other strains besides the ones deposited in connection with the present invention. It is to be understood that a blend of the invention may beside a strains deposited in connection with the invention also comprise other strains. One example is *Bacillus megaterium* SB-3112 (ATCC deposit number PTA-3142) disclosed in US 2005/0036990. In an embodiment the blends comprises NRRL B-50014, NRRL B-50015, NRRL B-50016, NRRL B-50017, NRRL B-50018 and PTA-3142.

Undesired Microorganisms

In context of the invention the term "undesired microorganisms" means microorganisms that may result in an effect considered to be negative on the surface in question and/or in the aqueous environment in question, especially in domestic or industrial settings. Examples of such negative effects include odor, corrosion, pitting, or other degradation of material; infection; staining or otherwise making a surface appear aesthetically unpleasing. Undesired microorganisms also include pathogenic microorganisms, especially pathogenic bacteria.

By using one or more of the isolated bacteria strains concerned herein in an effective amount biofilm formation on surfaces and/or planktonic proliferation in aqueous environments can be reduced and/or prevented.

In a preferred embodiment the surface in question prone to biofilm formation may be subjected to one or more of the bacteria strains as a preventative measure prior to any biofilm formation/buildup. This results in that significantly less biofilm is formed. Alternatively, if a biofilm has already formed, or at the first sign of biofilm buildup a method of the invention may be used to reduce further biofilm formation. A method of the invention may even result in partly or complete removal of the biofilm.

Examples of undesired microorganisms include those disclosed below.

Undesired microorganisms include, but are not limited to, aerobic bacteria or anaerobic bacteria, Gram positive and Gram negative, fungi (yeast or filamentous fungus), algae, and/or protozoa. Contemplated bacteria include bacteria selected from the group consisting of. *Pseudomonas* spp. including *Pseudomonas aeruginosa, Azotobacter vinelandii, Escherichia coli, Corynebacterium diphteriae, Clostridium botulinum, Streptococcus* spp., *Acetobacter, Leuconostoc, Betabacterium, Pneumococcus, Mycobacterium tuberculosis, Aeromonas, Burkholderia, Flavobacterium, Salmonella, Staphylococcus, Vibrio* spp., *Listeria* spp., and *Legionella* spp.

In a preferred embodiment, the undesired microorganism is an aerobic bacterium. In a more preferred embodiment, the aerobic bacterium is an *Aeromonas* strain. In another more preferred embodiment, the aerobic bacterium is a *Burkholderia* strain. In another more preferred embodiment, the aerobic bacterium is a *Flavobacterium* strain. In another more preferred embodiment, the aerobic bacterium is a *Microbacterium* strain. In another more preferred embodiment, the aerobic bacterium is a *Pseudomonas* strain. In another more preferred embodiment, the aerobic bacterium is a *Salmonella* strain. In another more preferred embodiment, the aerobic bacterium is a *Staphylococcus* strain. In another more preferred embodiment, the aerobic bacterium is from the family Enterobacteriaceae (including e.g., *Escherichia coli*).

In a most preferred embodiment, the aerobic bacterium is *Burkholderia cepacia*. In another most preferred embodiment, the aerobic bacterium is a *Microbacterium imperiale* or *Mycobacterium tuberculosis*. In another most preferred embodiment, the aerobic bacterium is *Pseudomonas aeruginosa*. In another most preferred embodiment, the aerobic bacterium is *Pseudomonas fluorescens*. In another most preferred embodiment, the aerobic bacterium is *Pseudomonas oleovorans*. In another most preferred embodiment, the aerobic bacterium is *Pseudomonas pseudoalcaligenes*. In another most preferred embodiment, the aerobic bacterium is *Salmonella enteritidis*. In another most preferred embodiment, the aerobic bacterium is *Staphylococcus aureus*. In another most preferred embodiment, the aerobic bacterium is *Staphylococcus epidermidis.*

In another most preferred embodiment the bacterium is *Listeria monocytogenes.*

In another most preferred embodiment the bacteria is *Legionella adelaidensis*. In another most preferred embodiment the bacteria is *Legionella pneumophila*. In another most preferred embodiment the bacteria is *Legionella feeleii*. In another most preferred embodiment the bacteria is *Legionella moravica*.

In another embodiment the bacteria is *Vibrio harveyi, Vibrio fischerii,* and/or *Vibrio alginolyticus*.

In another preferred embodiment, the microorganism is an anaerobic bacterium. In another more preferred embodiment, the anaerobic bacterium is a *Desulfovibrio* strain. In another most preferred embodiment, the anaerobic bacterium is *Desulfovibrio desulfuricans*.

In another preferred embodiment, the undesired microorganism is a fungus such as a yeast or filamentous fungus. In another more preferred embodiment, the yeast is a *Candida* strain. In another most preferred embodiment, the yeast is *Candida albicans*.

Composition of the Invention

The invention also relates to a composition comprising one or more of the deposited bacteria strains as described herein. It is to be understood that a composition of the invention may comprise one or more of the bacterial strains concerned herein as single strains or blends of two or more strains, but may also include other bacteria strains and/or active ingredients. In an embodiment the composition further comprises a surfactant or one or more other ingredients mentioned below.

Surfactants

The surfactants may be non-ionic including semi-polar and/or anionic and/or cationic and/or zwitterionic. The surfactant(s) should cause as little harm to the bacteria culture's activity as possible.

The surfactants may be present in the composition at a level of from 0.01% to 60% by weight.

When included therein the composition usually contains from about 0 to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the composition usually contains from about 0 to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

Other Ingredients

The composition may comprise one or more enzymes. Examples of contemplated enzymes are mentioned in the "Enzymes"-section.

Other ingredients include, but are not limited to, dispersants, stabilizers, anti-microbial agents, fragrances, dyes, and biocides.

Enzymes

One or more enzymes may be present in a composition of the invention. Especially contemplated enzymes include proteases, alpha-amylases, cellulases, lipases, peroxidases/oxidases, pectate lyases, and mannanases, or mixtures thereof.

Proteases:

Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274. Preferred commercially available protease enzymes include ALCALASE™, SAVINASE™, PRIMASE™, DURALASE™, DYRAZYM™, ESPERASE™, EVERLASE™, POLARZYME™ and KANNASE™, LIQUANASE™ (Novozymes A/S), MAXATASE™, MAXACAL™, MAXAPEM™, PROPERASE™, PURAFECT™, PURAFECT OxP™, FN2™, and FN3™ (Genencor International Inc.).

Lipases:

Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus* lipase, e.g., from *B. subtilis* (Dartois et al., 1993, Biochemica et Biophysica Acta 1131: 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include LIPOLASE™ and LIPOLASE ULTRA™, LIPOZYME™, and LIPEX™ (Novozymes A/S).

Cutinase:

The method of the invention may be carried out in the presence of cutinase classified in EC 3.1.1.74.

The cutinase used according to the invention may be of any origin. Preferably cutinases are of microbial origin, in particular of bacterial, of fungal or of yeast origin.

Cutinases are enzymes which are able to degrade cutin. In a preferred embodiment, the cutinase is derived from a strain of *Aspergillus*, in particular *Aspergillus oryzae*, a strain of *Alternaria*, in particular *Alternaria brassiciola*, a strain of *Fusarium*, in particular *Fusarium solani, Fusarium solani pisi, Fusarium roseum culmorum,* or *Fusarium roseum sambucium*, a strain of *Helminthosporum*, in particular *Helminthosporum sativum*, a strain of *Humicola*, in particular *Humicola insolens*, a strain of *Pseudomonas*, in particular *Pseudomonas mendocina*, or *Pseudomonas putida*, a strain of *Rhizoctonia*, in particular *Rhizoctonia solani*, a strain of *Streptomyces*, in particular *Streptomyces scabies*, or a strain of *Ulocladium*, in particular *Ulocladium consortiale*. In a most preferred embodiment the cutinase is derived from a strain of *Humicola insolens*, in particular the strain *Humicola insolens* DSM 1800. *Humicola insolens* cutinase is described in WO 96/13580 which is hereby incorporated by reference. The cutinase may be a variant, such as one of the variants disclosed in WO 00/34450 and WO 01/92502, which are hereby incorporated by reference. Preferred cutinase variants include variants listed in Example 2 of WO 01/92502, which is hereby specifically incorporated by reference.

Preferred commercial cutinases include NOVOZYM™ 51032 (available from Novozymes A/S, Denmark).

The method of the invention may be carried out in the presence of phospholipase classified as EC 3.1.1.4 and/or EC 3.1.1.32. As used herein, the term phospholipase is an enzyme which has activity towards phospholipids. Phospholipids, such as lecithin or phosphatidylcholine, consist of glycerol esterified with two fatty acids in an outer (sn-1) and the middle (sn-2) positions and esterified with phosphoric acid in the third position; the phosphoric acid, in turn, may be esterified to an amino-alcohol. Phospholipases are enzymes which participate in the hydrolysis of phospholipids. Several types of phospholipase activity can be distinguished, including phospholipases $A_1$ and $A_2$ which hydrolyze one fatty acyl group (in the sn-1 and sn-2 position, respectively) to form lysophospholipid; and lysophospholipase (or phospholipase B) which can hydrolyze the remaining fatty acyl group in lysophospholipid. Phospholipase C and phospholipase D (phosphodiesterases) release diacyl glycerol or phosphatidic acid respectively.

The term phospholipase includes enzymes with phospholipase activity, e.g., phospholipase A ($A_1$ or $A_2$), phospholipase B activity, phospholipase C activity or phospholipase D activity. The term "phospholipase A" used herein in connection with an enzyme of the invention is intended to cover an enzyme with Phospholipase $A_1$ and/or Phospholipase $A_2$ activity. The phospholipase activity may be provided by enzymes having other activities as well, such as, e.g., a lipase with phospholipase activity. The phospholipase activity may, e.g., be from a lipase with phospholipase side activity. In other embodiments of the invention the phospholipase enzyme activity is provided by an enzyme having essentially only phospholipase activity and wherein the phospholipase enzyme activity is not a side activity.

The phospholipase may be of any origin, e.g., of animal origin (such as, e.g., mammalian), e.g., from pancreas (e.g., bovine or porcine pancreas), or snake venom or bee venom. Preferably the phospholipase may be of microbial origin, e.g., from filamentous fungi, yeast or bacteria, such as the genus or species *Aspergillus*, e.g., *A. niger; Dictyostelium*, e.g., *D. discoideum; Mucor*, e.g., *M. javanicus, M. mucedo, M. subtilissimus; Neurospora*, e.g., *N. crassa; Rhizomucor*, e.g., *R. pusillus; Rhizopus*, e.g., *R. arrhizus, R. japonicus, R. stolonifer, Sclerotinia*, e.g., *S. libertiana; Trichophyton*, e.g., *T. rubrum; Whetzelinia*, e.g., *W. sclerotiorum; Bacillus*, e.g., *B. megaterium, B. subtilis; Citrobacter*, e.g., *C. freundii; Enterobacter*, e.g., *E. aerogenes, E. cloacae; Edwardsiella, E. tarda; Erwinia*, e.g., *E. herbicola; Escherichia*, e.g., *E. coli; Klebsiella*, e.g., *K. pneumoniae; Proteus*, e.g., *P. vulgaris; Providencia*, e.g., *P. stuartii; Salmonella*, e.g., *S. typhimurium; Serratia*, e.g., *S. liquefasciens, S. marcescens; Shigella*, e.g., *S. flexneri; Streptomyces*, e.g., *S. violeceoruber; Yersinia*, e.g., *Y. enterocolitica*. Thus, the phospholipase may be fungal, e.g., from the class Pyrenomycetes, such as the genus *Fusarium*, such as a strain of *F. culmorum, F. heterosporum, F. solani*, or a strain of *F. oxysporum*. The phospholipase may also be from a filamentous fungus strain within the genus *Aspergillus*, such as a strain of *Aspergillus awamori, Aspergillus foetidus, Aspergillus japonicus, Aspergillus niger* or *Aspergillus oryzae*.

Preferred phospholipases are derived from a strain of *Humicola*, especially *Humicola lanuginosa*. The phospholipase may be a variant, such as one of the variants disclosed in WO 00/32758, which are hereby incorporated by reference. Preferred phospholipase variants include variants listed in Example 5 of WO 00/32758, which is hereby specifically incorporated by reference. In another preferred embodiment the phospholipase is one described in WO 04/111216, especially the variants listed in the table in Example 1.

In another preferred embodiment the phospholipase is derived from a strain of *Fusarium*, especially *Fusarium oxysporum*. The phospholipase may be the one concerned in WO 98/026057 displayed in SEQ ID NO: 2 derived from *Fusarium oxysporum* DSM 2672, or variants thereof.

In a preferred embodiment of the invention the phospholipase is a phospholipase $A_1$ (EC. 3.1.1.32). In another preferred embodiment of the invention the phospholipase is a phospholipase $A_2$ (EC.3.1.1.4.).

Examples of commercial phospholipases include LECITASE™ and LECITASE™ ULTRA, YIELSMAX, or LI POPAN F (available from Novozymes A/S, Denmark).

Amylases:

Suitable amylases (alpha and/or beta) include those of bacterial or fungal origin. Chemically modified or protein engineered mutants are included. Amylases include, for example, alpha-amylases obtained from *Bacillus*, e.g., a special strain of *B. licheniformis*, described in more detail in GB 1,296,839, or the *Bacillus* sp. strains disclosed in WO 95/026397 or WO 00/060060.

Examples of useful amylases are the variants described in WO 94/02597, WO 94/18314, WO 96/23873, WO 97/43424, WO 01/066712, WO 02/010355, WO 02/031124 and WO 2006/002643 (which references all incorporated by reference.

Commercially available amylases are DURAMYL™, TERMAMYL™, TERMAMYL ULTRA™, NATALASE™, STAINZYME™, STAINZYME ULTRA™, FUNGAMYL™ and BAN™ (Novozymes A/S), RAPIDASE™ and PURASTAR™ (from Genencor International Inc.).

Cellulases:

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Thielavia terrestris, Myceliophthora thermophila*, and *Fusarium oxysporum* disclosed in U.S. Pat. No. 4,435,307, U.S. Pat. No. 5,648,263, U.S. Pat. No. 5,691,178, U.S. Pat. No. 5,776,757, WO 89/09259, WO 96/029397, and WO 98/012307. Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and WO 1999/001544.

Commercially available cellulases include CELLUZYME™, CELLUCLAST™, CAREZYME™, ENDOLASE™, RENOZYME™ (Novozymes A/S), CLAZINASE™ and PURADAX HA™, ACCELERASE™ 1000 (Genencor International Inc.), and KAC-500(B)™ (Kao Corporation).

Peroxidases/Oxidases:

Suitable peroxidases/oxidases include those of plant, bacterial or fungal origin. Chemically modified or protein engineered mutants are included. Examples of useful peroxidases include peroxidases from *Coprinus*, e.g., from *C.*

*cinereus*, and variants thereof as those described in WO 93/24618, WO 95/10602, and WO 98/15257.

Commercially available peroxidases include Guardzyme™ and Novozym™ 51004 (Novozymes A/S).

Pectate Lyases (Also Called Polygalacturonate Lyases):

Examples of pectate lyases include pectate lyases that have been cloned from different bacterial genera such as *Erwinia, Pseudomonas, Klebsiella* and *Xanthomonas*, as well as from *Bacillus subtilis* (Nasser et al., 1993, *FEBS Letts.* 335:319-326) and *Bacillus* sp. YA-14 (Kim et al., 1994, *Biosci. Biotech. Biochem.* 58: 947-949). Purification of pectate lyases with maximum activity in the pH range of 8-10 produced by *Bacillus pumilus* (Dave and Vaughn, 1971, *J. Bacteriol.* 108: 166-174), *B. polymyxa* (Nagel and Vaughn, 1961, *Arch. Biochem. Biophys.* 93: 344-352), *B. stearothermophilus* (Karbassi and Vaughn, 1980, *Can. J. Microbiol.* 26: 377-384), *Bacillus* sp. (Hasegawa and Nagel, 1966, *J. Food Sci.* 31: 838-845) and *Bacillus* sp. RK9 (Kelly and Fogarty, 1978, *Can. J. Microbiol.* 24: 1164-1172) have also been described. Any of the above, as well as divalent cation-independent and/or thermostable pectate lyases, may be used in practicing the invention. In preferred embodiments, the pectate lyase comprises the amino acid sequence of a pectate lyase disclosed in Heffron et al., 1995, *Mol. Plant-Microbe Interact.* 8: 331-334 and Henrissat et al., 1995, *Plant Physiol.* 107: 963-976. Specifically contemplated pectate lyases are disclosed in WO 99/27083 and WO 99/27084. Other specifically contemplated pectate lyases derived from *Bacillus licheniformis* is disclosed as SEQ ID NO: 2 in U.S. Pat. No. 6,284,524 (which document is hereby incorporated by reference). Specifically contemplated pectate lyase variants are disclosed in WO 02/006442, especially the variants disclosed in the Examples in WO 02/006442 (which document is hereby incorporated by reference).

Examples of commercially available alkaline pectate lyases include BIOPREP™ and SCOURZYME™ L from Novozymes A/S, Denmark.

Mannanase:

Examples of mannanases (EC 3.2.1.78) include mannanases of bacterial and fungal origin. In a specific embodiment the mannanase is derived from a strain of the filamentous fungus genus *Aspergillus*, preferably *Aspergillus niger* or *Aspergillus aculeatus* (WO 94/25576). WO 93/24622 discloses a mannanase isolated from *Trichoderma reesei*. Mannanases have also been isolated from several bacteria, including *Bacillus* organisms. For example, Talbot et al., 1990, *Appl. Environ. Microbiol.* 56(11): 3505-3510 describes a beta-mannanase derived from *Bacillus stearothermophilus*. Mendoza et al., 1994, *World J. Microbiol. Biotech.* 10(5): 551-555 describes a beta-mannanase derived from *Bacillus subtilis*. JP-A-03047076 discloses a beta-mannanase derived from *Bacillus* sp. JP-A-63056289 describes the production of an alkaline, thermostable beta-mannanase. JP-A-63036775 relates to the *Bacillus* microorganism FERM P-8856 which produces beta-mannanase and beta-mannosidase. JP-A-08051975 discloses alkaline beta-mannanases from alkalophilic *Bacillus* sp. AM-001. A purified mannanase from *Bacillus amyloliquefaciens* is disclosed in WO 97/11164. WO 91/18974 describes a hemicellulase such as a glucanase, xylanase or mannanase active. Contemplated are the alkaline family 5 and 26 mannanases derived from *Bacillus agaradhaerens, Bacillus licheniformis, Bacillus halodurans, Bacillus clausii, Bacillus* sp., and *Humicola insolens* disclosed in WO 99/64619. Especially contemplated are the *Bacillus* sp. mannanases concerned in the Examples in WO 99/64619 which document is hereby incorporated by reference.

Examples of commercially available mannanases include MANNAWAY™ available from Novozymes A/S Denmark.

Materials & Methods

Chemicals used as buffers and reagents were commercial products of at least reagent grade.

Plate Count Broth (Difco 275120)
MacConkey agar (Smith River Biologicals, Ferrum, Va. cat#11-00380)
Luria Broth (Difco 241420)
Standard Methods agar plates (SMA plates) (Smith River Biologicals, Ferrum, Va. cat#11-00450)

Bacteria Strains:

*Bacillus* Blend (6BB): Blend of six *Bacillus* spp. strains consisting of the following deposited strains: NRRL# B-50014 (30%), B-50015 (30%), B-50016 (10%), B-50017 (10%), B-50018 (10%), B-50019 (10%). The actual ratio between the strains in the 6BB blend is indicated in parenthesis (x %).

*Pseudomonas aeruginosa*: The *Pseudomonas aeruginosa* strain used in all Examples equipped with a plasmid expressing green fluorescent protein constitutively was constructed as described by Nivens et al., 2001, *J. Bacteriol.* 183: 1047-1057.

*Pseudomonas montelli* (ATCC 700412)
*Pseudomonas putida* (ATCC 49451)
*Vibrio harveyi* (ATCC 25919)
*Vibrio alginolyticus* (ATCC 17749)
*Vibrio fisherii* (MJ-1): wild-type strain Deposit of Biological Material Biological material has been deposited under the terms of the Budapest Treaty at American Type Culture Collection (ATCC), 10801 University Blvd., Manassas, Va. 20108, USA., and
Microbial Genomics and Bioprocessing Research Unit (NRRL) National Center for Agricultural Utilization Research 1815 N. University Street, Peoria, Ill. 61604, USA.

The bacteria strains were given the following accession #:

| Identification | Accession Number | Date of Deposit |
|---|---|---|
| *Bacillus amyloliquefaciens* | PTA-7541 | 20 Apr. 2006 |
| *Bacillus amyloliquefaciens* | PTA-7542 | 20 Apr. 2006 |
| *Bacillus atrophaeus* | PTA-7543 | 20 Apr. 2006 |
| *Bacillus amyloliquefaciens* | PTA-7544 | 20 Apr. 2006 |
| *Bacillus amyloliquefaciens* | PTA-7545 | 20 Apr. 2006 |
| *Bacillus amyloliquefaciens* | PTA-7546 | 20 Apr. 2006 |
| *Bacillus subtilis* subsp. *subtilis* | PTA-7547 | 20 Apr. 2006 |
| *Bacillus velezensis* | PTA-7548 | 20 Apr. 2006 |
| *Bacillus amyloiquefaciens* | PTA-7549 | 20 Apr. 2006 |
| *Bacillus simplex* | PTA-7550 | 20 Apr. 2006 |
| *Bacillus simplex* | PTA-7789 | 18 Aug. 2006 |
| *Bacillus amyloliquefaciens* | PTA-7790 | 18 Aug. 2006 |
| *Bacillus amyloliquefaciens* | PTA-7791 | 18 Aug. 2006 |
| *Bacillus atrophaeus* | PTA-7792 | 18 Aug. 2006 |
| *Bacillus amyloliquefaciens* | PTA-7793 | 18 Aug. 2006 |
| *Bacillus amyloliquifaciens* | NRRL B-50017 | 14 Mar. 2007 |
| *Bacillus megaterium* | NRRL B-50019 | 14 Mar. 2007 |
| *Bacillus amyloliquifaciens* | NRRL B-50018 | 14 Mar. 2007 |
| *Bacillus licheniformis* | NRRL B-50014 | 14 Mar. 2007 |
| *Bacillus licheniformis* | NRRL B-50015 | 14 Mar. 2007 |
| *Bacillus pumilus* | NRRL B-50016 | 14 Mar. 2007 |

The strains have been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposits represent pure cultures. The deposits are available as required by foreign patent laws in countries wherein counterparts of the subject application or its progeny are filed. However, it should be understood that the availability of a deposit does not constitute a license to practice the subject invention in derogation of patent rights granted by governmental action.

The bacteria strains deposited at ATTC are derived from isolated naturally occurring bacteria strains. All strains were collected in the United States in 2005.

For the bacteria strains deposited at NRRL two were collected from soil in the United States (deposited as NRRL B-50017 and NRRL B-50018) and four came from US culture collections. To the best of our belief NRRL B-50014 is the same as ATCC #23842; NRRL B-50015 is the same as ATCC #21415; NRRL B-50016 is the same as NRRL B-4064; and NRRL B-50019=NRRL B3254).

The strains may consist of dormant bacteria spores and/or viable bacteria.

Equipment:

Fluorescent kinetic microtiter plate reader (BioTek Synergy HT-I)

Polycarbonate holder (Biosurfaces Technology, USA)

Porcelain coupons (Tyler Research Instruments Corp., Edmonton, Alberta, Canada)

Wide-mouth test tube (Fisher cat#NC9421998, Pittsburg, Pa., USA)

EXAMPLES

Example 1

Planktonic Proliferation of *Pseudomonas* in the Presence of *Bacillus* Blend (6BB)—Fluorescent Microtiter Plate (FMP)

Wells of a 96-microtiter plate were filled with 200 microL of Plate Count Broth (Difco DF0751-17-2) and inoculated with a *Pseudomonas aeruginosa* strain equipped with a plasmid expressing green fluorescent protein constitutively. A blend of six *Bacillus* spp. (6BB) was added to the wells. Initial dose of *Pseudomonas* was either $2.4 \times 10^8$ or $4.8 \times 10^8$ cfu/mL while *Bacillus* spp. dose was $6.8 \times 10^6$ to $1.0 \times 10^7$ cfu/mL resulting in *Pseudomonas*:*Bacillus* ratios of 24:1 and 70:1. Microtiter plates were tracked with a fluorescent kinetic microtiter plate reader (BioTek Synergy HT-I) with incubation at 21° C. and fluorescent reads at 485/20 nm excitation, 528/20 nm emission, every 20 minutes for 43 hours. Resulting fluorescence kinetic curves showed *Bacillus*-dose dependent suppression of gfp fluorescence (i.e., *Pseudomonas* population suppression) (FIG. 1).

Example 2

Reduced *Pseudomonas* Biofilm Formation and Planktonic Proliferation in Presence of *Bacillus* Blend—Test Tube+ Coupon Biocontrol (TTCBC)

A polycarbonate holder (Biosurfaces Technology) with three porcelain coupons (Tyler Research Instruments Corp., Edmonton, Alberta) was inserted into a wide-mouth test tube (Fisher cat#NC9421998) and 50 mL Plate Count Broth (Difco DF0751-17-2) made according to label instructions was added and autoclaved. Tubes were inoculated with a blend of *Bacillus* spores and incubated at 28° C. with mild shaking overnight thereby allowing germination. Initial dose of *Bacillus* spores ranged from $2.6 \times 10^2$ to $7.8 \times 10^5$ cfu/mL.

Figure 2:
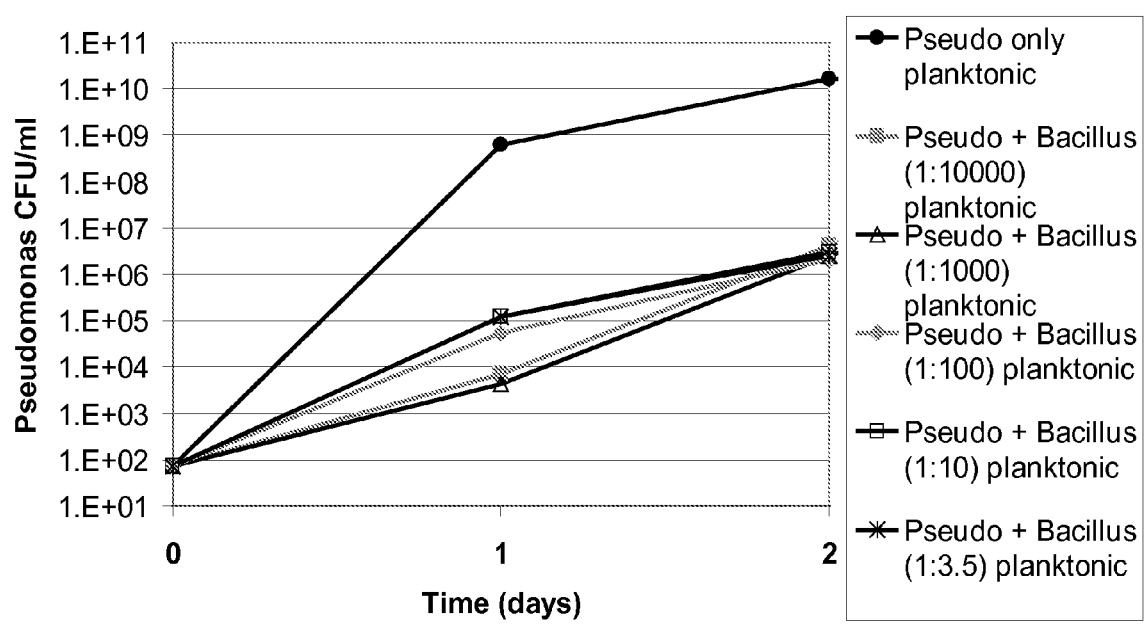
FIG. 2 shows reduced *Pseudomonas* biofilm populations in the presence of *Bacillus* blend (6BB) at different *Bacillus:Pseudomonas* ratios.
Figure 3:
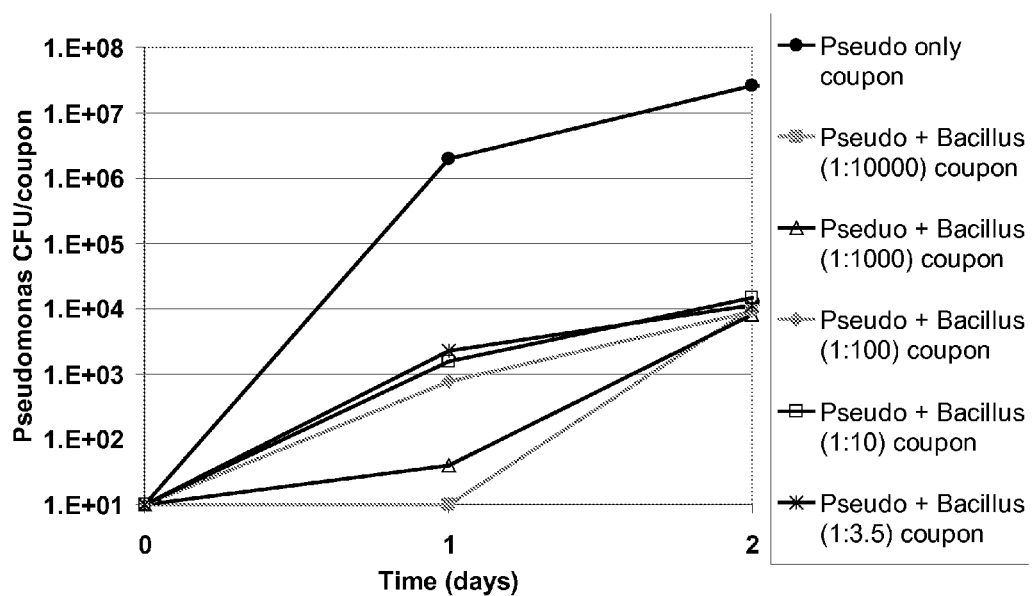
FIG. 3 shows reduced planktonic *Pseudomonas* proliferation in the presence of *Bacillus* blend (6BB) at different *Bacillus:Pseudomonas* ratios.

The following day, a *Pseudomonas aeruginosa* strain with gfp expression was added to the tubes at a concentration of 70 cfu/ml resulting in *Pseudomonas*:*Bacillus* initial inoculum ratios ranging from 1:3.5 to 1:10,000. Following additional 24 and 48 hour periods of incubation, the tubes were destructively sampled by scraping each coupon (biofilm cells) into phosphate buffered saline, homogenizing the suspension, then diluting and plating on MacConkey agar (Difco DF0075-17-1) to enumerate only *Pseudomonas* cells. The broth in the tubes (planktonic cells) was also sampled, diluted and plated. *Pseudomonas* counts in the presence of *Bacillus* spp. were compared to negative controls with no *Bacillus* spp. present and it was noted that *Bacillus* spp. treatment resulted in significant and roughly dose dependent reduction of *Pseudomonas* populations in biofilm (FIG. 2) and planktonic (FIG. 3) states.

Example 3

Reduced *Pseudomonas* Biofilm Formation and Planktonic Proliferation in Presence of *Bacillus* Isolates—Test Tube+ Coupon Biocontrol (TTCBC)

A polycarbonate holder (Biosurfaces Technology) with three porcelain coupons (Tyler Research Instruments Corp., Edmonton, Alberta) was inserted into a wide-mouth test tube (Fisher cat#NC9421998) and 50 mL Plate Count Broth (Difco DF0751-17-2) made according to label instructions was added and autoclaved. Each tube was inoculated with an overnight vegetative cell culture of an individual *Bacillus* candidate and an overnight culture of *Pseudomonas aeruginosa* equipped with a gfp plasmid. The tubes were incubated at 28° C. with mild shaking. Initial dose of *Bacillus* cells was in the range of $1.0 \times 10^3$ to $8.2 \times 10^5$ cfu/mL and initial dose of *Pseudomonas* was approximately $1 \times 10^3$ to $1 \times 10^5$. The *Pseudomonas* to *Bacillus* ratios ranged from 1:2 to 1:147.

At time points 24 and 48 hours into incubation, the tubes were destructively sampled by scraping each coupon (biofilm cells) into phosphate buffered saline, homogenizing the suspension, then diluting and plating on MacConkey agar (Difco DF0075-17-1) to enumerate only *Pseudomonas* cells. The broth in the tubes (planktonic cells) was also sampled, diluted and plated. *Pseudomonas* counts in the presence of *Bacillus* spp. were compared to negative controls with no *Bacillus* spp. present and log control of *Pseudomonas* for each *Bacillus* candidate was calculated at time 24 and 48 hours for planktonic and attached cells.

| Strain | P:B ratio 1:x B | Log control 24 hr planktonic | Log control 24 hr attached | Log control 48 hr planktonic | Log control 48 hr attached |
|---|---|---|---|---|---|
| PTA-7544 | 9.5 | 3.4 | 2.2 | 5.4 | 4.1 |
| PTA-7790 | 22.8 | 3.0 | 1.9 | 5.1 | 4.4 |
| PTA-7791 | 85 | 4.8 | 2.7 | 4.5 | 4.8 |
| PTA-7792 | 4.2 | 3.2 | 3.0 | 5.4 | 4.0 |
| PTA-7549 | 147.1 | 4.5 | 3.7 | 6.0 | 4.3 |
| PTA-7542 | 2.8 | 2.9 | 2.8 | 5.8 | 4.5 |
| PTA-7545 | 3.7 | 3.6 | 3.2 | 7.1 | 5.3 |
| NRRL B-50017 | 2.3 | 3.1 | 2.4 | 5.8 | 4.4 |
| NRRL B-50016 | 4.8 | 0.9 | 1.4 | 0.6 | 0.5 |

Example 4

Reduced *E. coli* Biofilm Formation and Planktonic Proliferation in Presence of *Bacillus* Isolates—Test Tube+Coupon Biocontrol (TTCBC)

A polycarbonate holder (Biosurfaces Technology) with three porcelain coupons was inserted into a wide-mouth test tube (Fisher cat#NC9421998) and 50 mL plate count broth (Difco DF0751-17-2) made according to label instructions was added and autoclaved. Each tube was inoculated with an overnight vegetative cell culture of an individual *Bacillus* candidate and an overnight culture of *E. coli*. The tubes were incubated at 28° C. with mild shaking. Initial dose of *Bacillus* cells was in the range of $1.0 \times 10^3$ to $8.2 \times 10^5$ cfu/mL and initial dose of *E. coli* was in the range of $1 \times 10^3$ to $1 \times 10^5$. The *E. coli* to *Bacillus* ratios ranged from 1:0.6 to 1:32.

At time points 24 and 48 hours into incubation, the tubes were destructively sampled by scraping each coupon (biofilm cells) into phosphate buffered saline, homogenizing the suspension, then diluting and plating on MacConkey agar (Difco DF0075-17-1) to enumerate only *E. coli* cells. The broth in the tubes (planktonic cells) was also sampled, diluted and plated. *E. coli* counts in the presence of *Bacillus* spp. were compared to negative controls with no *Bacillus* spp. present and log control of *E. coli* for each *Bacillus* candidate was calculated at time 24 and 48 hours for planktonic and attached cells.

| Strain | P:B ratio | Log control 24 hour planktonic | Log control 24 hour attached | Log control 48 hour planktonic | Log control 48 hour attached |
|---|---|---|---|---|---|
| PTA-7544 | 2.7 | 4.4 | 5.2 | >9 | >9 |
| PTA-7790 | 21.0 | 5.2 | 6.3 | >9 | >9 |
| PTA-7791 | 2.8 | 2.5 | 2.1 | 7.3 | 4.2 |
| PTA-7792 | 2.3 | 0.0 | 0.6 | 0.0 | 0.0 |
| PTA-7549 | 0.8 | 5.2 | 6.8 | 9.7 | 6.5 |
| PTA-7542 | 5.7 | 5.1 | 4.7 | >9 | 5.4 |
| PTA-7545 | 17.0 | 5.1 | 4.9 | >9 | >9 |
| NRRL B-50017 | 0.6 | 3.7 | 4.1 | 8.7 | 7.4 |
| PTA-7546 | 32.4 | 4.0 | 3.9 | 9.7 | 7.2 |

Example 5

Petri Plate *E. coli* Zone of Inhibition

*Bacillus* candidates were grown in Plate Count broth for 18 to 24 hours resulting in appx $10^7$ to $10^8$ cfu/mL. *E. coli* grown 18 to 24 hours (appx $10^8$ to $10^{10}$ cfu·mL) was streaked to form a lawn on the surface of Standard Methods agar plates (SMA plates) Smith River Biologicals, Ferrum, Va.) and four 5 mm holes were bored into the agar with a sterile stainless steel tube. 50 microL of each *Bacillus* liquid culture was delivered into the holes (1 strain per hole) and the plate was incubated for 18 to 48 hours at 35° C., agar side down. Inhibited *E. coli* lawn in proximity to a hole was scored as positive biocontrol for the *Bacillus* candidate. The zone of inhibition was measured in millimeters (mm) to allow semi-quantitative assessment of control. Discernable inhibition >1 mm was scored as a positive.

| Strain | *E. coli* inhibition |
|---|---|
| NRRL B-50016 | − |
| NRRL B-50017 | − |
| PTA-7541 | + |
| PTA-7792 | + |
| PTA-7542 | + |
| PTA-7543 | + |
| PTA-7544 | + |
| PTA-7545 | + |
| PTA-7546 | + |
| PTA-7547 | − |
| PTA-7549 | + |
| PTA-7791 | + |
| PTA-7790 | + |

Example 6

Petri Plate *Pseudomonas aeruginosa* Zone of Inhibition

*Bacillus* candidates were grown in Plate Count broth for 18 to 24 hours resulting in appx $10^7$ to $10^8$ cfu/mL culture. *Pseudomonas aeruginosa* was grown 18 to 24 hours (appx $10^8$ to $10^{10}$ cfu/mL) and streaked to form a lawn on the surface of Standard Methods agar plates (Smith River Biologicals, Ferrum, Va.) and four 5 mm holes were bored into the agar with a sterile stainless steel tube. 50 microL of each *Bacillus* liquid culture were delivered into the holes (1 strain per hole) and the plate was incubated for 18 to 48 hours at 35° C., agar side down. Inhibited *Pseudomonas* lawn in proximity to a hole was scored as positive biocontrol for the *Bacillus* candidate. The zone of inhibition was also measured in micrometers (mm) to allow semi-quantitative assessment of control.

Discernable inhibition >0.5 mm was scored as a positive.

| Strain | *Pseudomonas aeruginosa* inhibition |
|---|---|
| NRRL B-50016 | − |
| NRRL B-50017 | + |
| PTA-7542 | + |
| PTA-7545 | + |
| PTA-7791 | + |

Example 7

Petri Plate *Pseudomonas montelli* and *Putida* Zone of Inhibition

*Bacillus* candidate NRRL B-50014 was grown in Plate Count broth for 18 to 24 hours resulting in appx $10^7$ to $10^8$ cfu/mL culture. *Pseudomonas montelli* (ATCC 700412) and *Ps. putida* (ATCC 49451) grown 18 to 24 hours (appx $10^8$ to $10^{10}$ cfu/ml culture) were streaked to form a lawn on the surface of Standard Methods agar plates and four 5 mm holes were bored into the agar with a sterile stainless steel tube. 50 microL of *Bacillus* liquid culture were delivered into the holes and the plate was incubated for 18 to 48 hours at 35° C., agar side down. Inhibited *Pseudomonas* lawn in proximity to a hole was scored as positive biocontrol for the *Bacillus* candidate. The zone of inhibition was also measured in millimeters (mm) to allow semi-quantitative assessment of control.

Discernable inhibition >1 mm was scored as a positive.

| Strain | *Pseudomonas monteilli* inhibition | *Pseudomonas putida* inhibition |
|---|---|---|
| NRRL B-50014 | + | + |

Example 8

Quorum Sensing Inhibition

*Serratia rubidaea* (ATCC 27593) was used as the indicator bacterium as its pigmentation is dependent on in tact quorum sensing pathway. Quorum sensing compounds allow bacteria to "communicate" and affect phenotypes such as pigmentation, motility, pathogenicity and biofilm formation, thus Quorum Sensing Inhibition is a mode of action for biofilm control.

*Bacillus* candidates were grown in plate count broth, 18 to 24 hours, 35° C., to a density of appx. $10^7$ cfu/mL. The *Bacilli* were spotted (10 microL) onto a Standard Methods agar plate (Smith River Biologicals, Ferrum, Va.) and incubated for 18 to 24 hours at 26° C., after which time, colonies were visible. The *Serratia* culture (5 microL) (Luria broth, 18 to 24 hours, 26° C., appx. $10^7$ cfu/ml) was added to 5 mL of 0.5% molten LB agar (Luria broth 30.5 g/L and 0.5% noble agar), mixed well, and poured over the plates with mature *Bacillus* candidate colonies. After the agar set, the plate was incubated 18 to 24 hours at 26° C. Zones of inhibited pigmentation but not inhibited *Serratia* growth per se were scored positive for QSI and measured across their full diameter for semi-quantitative results.

| Strain | Diameter of suppressed pigmentation (mm) |
|---|---|
| NRRL B-50014 | 27 |
| NRRL B-50015 | 27 |
| NRRL B-50016 | 45 |
| NRRL B-50017 | 42 |
| NRRL B-50018 | 36 |
| PTA-7541 | 39 |
| PTA-7792 | 43 |
| PTA-7542 | 31 |
| PTA-7543 | 24 |
| PTA-7544 | 49 |

-continued

| Strain | Diameter of suppressed pigmentation (mm) |
|---|---|
| PTA-7545 | — |
| PTA-7546 | 43 |
| PTA-7547 | 28 |
| PTA-7548 | — |
| PTA-7549 | 50 |
| PTA-7793 | — |
| PTA-7790 | — |
| PTA-7791 | 40 |

Example 9

Control of *Pseudomonas* Biofilm and Planktonic Cell Proliferation in Presence of *Bacillus* Candidate in CDC Biofilm Reactors CDC Biofilm reactors (Biosurfaces Technologies, Bozeman, Mont., Cat#CBR90-2) with porcelain coupons (Tyler Research Instruments Corp., Edmonton, Alberta) were filled with 400 ml plate count broth and autoclaved. PTA-7546 spores were added to the cooled media of two reactors (initial dose=$4.5 \times 10^5$ cfu/mL in reactor) to allow 24 hour pregermination time with room temperature incubation, stir bar set to 60 rpm before *Pseudomonas* insult. Two additional reactors were treated as controls without *Bacillus* inoculation. *Pseudomonas aeruginosa* was grown overnight in plate count broth and 20 microL of a 1:100 dilution of *Pseudomonas* culture was then added to all four reactors (3590 cfu/mL) and the resulting co-culture ratio was 1 *Pseudomonas*:127 *Bacilli*. After 24 hours of growth, media redosing began at a rate of 3 mL/min dilute plate count broth (1 g/L concentration). Stirring was set to 60 rpm.

One day later (two days after co-culture began), liquid samples were taken from each reactor, diluted and plated on Maconkey agar and incubated appx. 18 hours at 35° C. to obtain Gram negative (=*Pseudomonas*=undesirable organism) count. Similarly, coupons were scraped with sterile wooden applicator sticks and the scrapings were suspended in sterile phosphate buffer, homogenized, and diluted and plated on MacConkey agar which was incubated for 18 hours at 35° C. Comparison of *Pseudomonas* counts in treated vs. untreated reactors allowed calculation of "log control in *Bacillus* reactors".

| Condition | Treated reactor A † | Treated reactor B † | Average treated reactors † | Untreated reactor A † | Untreated reactor B † | Average untreated reactors † | Average log control † |
|---|---|---|---|---|---|---|---|
| Biofilm (scraped from coupons) | $2.6 \times 10^2$ | $5.7 \times 10^2$ | $4.2 \times 10^2$ | $6.7 \times 10^6$ | $1.4 \times 10^6$ | $4.1 \times 10^6$ | 3.9 |
| Planktonic (liquid) samples | $1.4 \times 10^4$ | $1.1 \times 10^4$ | $1.3 \times 10^4$ | $2.1 \times 10^7$ | $6.4 \times 10^7$ | $4.3 \times 10^7$ | 3.5 |

† count cfu/mL or cfu/coupon

Example 10

Control of *Pseudomonas* Biofilm and Planktonic Cell Proliferation in Presence of *Bacillus* Candidate in CDC Biofilm Reactors with *Bacillus* Spore Redosing CDC Biofilm reactors (Biosurfaces Technologies, Bozeman, Mont., Cat#CBR90-2) with porcelain coupons (Tyler Research Instruments Corp., Edmonton, Alberta) were filled with 400 mL plate count broth (full strength) and autoclaved. PTA-7545 (trial 1) or NRRL B-50017 (trial 2) spores were added to the cooled media of two reactors to allow 24 hour pregermination time at room temperature with 60 rpm stir bar stirring, before *Pseudomonas* insult (initial *Bacillus* dose=$1.3 \times 10^5$ cfu/ml in reactor trial 1, 1012 cfu/ml trial 2). Two additional reactors were treated as controls without Bacillus inoculation. Pseudomonas aeruginosa was grown overnight in plate count broth and 20 microL of a 1:100 dilution of Pseudomonas culture was added to all four reactors (127 cfu/ml trial 1, 1×10$^5$ cfu/ml trial 2) and the resulting co-culture ratio was 1 Pseudomonas:104 Bacilli for trial 1 and 1:0.1 for trial 2. After 24 hours of growth, media redosing began at a rate of 90 ml/15 min dilute plate count broth (1 g/L concentration) for 15 min every hour. For the treated reactors, Bacillus spores were dosed at a rate of 1.5 ml spore concentrate over the course of 2.7 hours for a final concentration of 1.1×10$^8$ cfu Bacillus spores/day for trial 1 and 1.8×10$^7$ cfu Bacillus spores/day for trial 2. Stirring was set to 60 rpm.

One day later (two days after co-culture began), liquid samples were taken from each reactor, diluted and plated on Maconkey agar and incubated appx. 18 hours at 35° C. to obtain Gram negative (undesirable organism) count. Similarly, coupons were scraped with sterile wooden applicator sticks and the scrapings were suspended in sterile phosphate buffer, homogenized and diluted and plated on MacConkey agar which was incubated for 18 hours at 35° C. Comparison of Pseudomonas counts in treated vs. untreated reactors allowed calculation of "log control in Bacillus reactors".

| Condition | PTA-7545 Average log control | NRRL B-50017 Average log control |
|---|---|---|
| Biofilm (scraped from coupons) | 4.5 | 2.9 |
| Planktonic (liquid) samples | 4.4 | 3.5 |

Example 11

Petri Plate *Vibrio harveyi* Zone of Inhibition

Bacillus candidates were grown in nutrient broth (3 g/L beef extract, 5 g/L peptone) at 35° C. for 18-24 hours. *V. harveyi* ATCC 25919 was grown in nutrient broth with 1.5% added NaCl at 28° C. for 18-24 hours. Nutrient agar (1.5% agar) with 1.5% NaCl was autoclaved in 25 mL aliquots and 250 microL overnight *Vibrio* culture was added to each aliquot of molten agar resulting in approximately 1×10$^6$ cfu/mL *Vibrio* in agar. After agar solidified, 4 holes were bored in each plate using a piece of sterilized stainless steel tubing. 50 microL of each overnight Bacillus culture was transferred to each well. Plates were incubated agar side down at 28° C. for 18-24 hours. Zones of inhibited *Vibrio* lawn were measured. Discernable inhibition >0.5 mm was scored as a positive.

| Strain | *Vibrio harveyi* |
|---|---|
| NRRL B-50015 | + |
| NRRL B-50016 | + |
| NRRL B-50017 | + |
| PTA-7542 | + |
| PTA-7543 | + |
| PTA-7544 | + |
| PTA-7545 | + |
| PTA-7546 | + |
| PTA-7547 | + |
| PTA-7548 | + |
| PTA-7749 | + |
| PTA-7793 | + |
| PTA-7790 | + |
| PTA-7791 | + |

Example 12

Petri Plate *Vibrio alginolyticus* Zone of Inhibition

Bacillus candidates were grown in nutrient broth (3 g/L beef extract, 5 g/L peptone) at 35° C. for 18-24 hours. *V. alginolyticus* ATCC 17749 was grown in nutrient broth with 1.5% added NaCl at 28° C. for 18-24 hours. Nutrient agar (1.5% agar) with 1.5% NaCl was autoclaved in 25 mL aliquots and 250 microL overnight *Vibrio* culture was added to each aliquot of molten agar resulting in approximately 1×10$^6$ cfu/ml *Vibrio* in agar. After agar solidified, 4 holes were bored in each plate using a piece of sterilized stainless steel tubing. 50 microL of each overnight Bacillus culture was transferred to each well. Plates were incubated agar side down at 28° C. for 18-24 hours. Zones of inhibited *Vibrio* lawn were measured. Discernable inhibition >0.5 mm was scored as a positive.

| Strain | *Vibrio alginolyticus* |
|---|---|
| NRRL B-50015 | + |
| NRRL B-50016 | + |
| NRRL B-50017 | + |
| PTA-7541 | + |
| PTA-7592 | + |
| PTA-7542 | + |
| PTA-7543 | + |
| PTA-7544 | + |
| PTA-7545 | + |
| PTA-7546 | + |
| PTA-7747 | + |
| PTA-7748 | + |
| PTA-7749 | + |
| PTA-7793 | + |
| PTA-7790 | + |
| PTA-7791 | + |

Example 13

Petri Plate *Vibrio fischerii* Zone of Inhibition

Bacillus candidates were grown in nutrient broth (3 g/L beef extract, 5 g/L peptone) at 35° C. for 18-24 hours. *V. fisherii* was grown in nutrient broth with 1.5% added NaCl at 28° C. for 18-24 hours. Nutrient agar (1.5% agar) with 1.5% NaCl was autoclaved in 25 mL aliquots and 250 microL overnight *Vibrio* culture was added to each aliquot of molten agar resulting in approximately 1×10$^6$ cfu/ml *Vibrio* in agar. After agar solidified, 4 holes were bored in each plate using a piece of sterilized stainless steel tubing. 50 microL of each overnight Bacillus culture was transferred to each well. Plates were incubated agar side down at 28° C. for 18-24 hours. Zones of inhibited *Vibrio* lawn were measured. Discernable inhibition >0.5 mm was scored as a positive.

| Strain | *Vibrio fischerii* |
|---|---|
| PTA-7543 | + |
| PTA-7545 | + |
| PTA-7546 | + |
| PTA-7547 | + |
| PTA-7548 | + |
| PTA-7793 | + |
| PTA-7790 | + |
| PTA-7791 | + |

The invention claimed is:
1. A method for preventing and/or reducing biofilm formation on a surface, comprising subjecting the surface to one or more bacterial strains, wherein the one or more bacterial strains comprise:

the strain having the deposit accession number NRRL B-50017;
the strain having the deposit accession number PTA-7541;
the strain having the deposit accession number PTA-7542;
the strain having the deposit accession number PTA-7543;
the strain having the deposit accession number PTA-7545;
the strain having the deposit accession number PTA-7546;
the strain having the deposit accession number PTA-7791; or
a mixture of two or more of the strains;
wherein the biofilm formation is other than *E. coli* biofilm formation.

2. The method of claim 1, wherein the surface is made of one or more materials selected from the group consisting of metal, plastics, rubber, board, glass, wood, paper, concrete, rock, marble, gypsum, and ceramic materials.

3. The method of claim 1, wherein the surface is on a toilet bowl; a toilet water reservoir; a cooling tower; a water treatment plant; a water tank; a food processing plant; a chemical or pharmaceutical process plant; or a medical device.

4. The method of claim 1, wherein the biofilm formation is caused by *Pseudomonas*.

5. The method of claim 1, wherein the method is repeated periodically.

6. The method of claim 1, further comprising subjecting the surface to an enzyme selected from the group of alpha-amylases, cellulases, lipases, mannanases, oxidases, pectate lyases, peroxidases, and proteases, or a mixture thereof.

7. The method of claim 1, further comprising subjecting the surface to one or more agents selected from the group consisting of dispersants, surfactants, anti-microbial agents, and biocides.

8. The method of claim 1, wherein the one or more bacterial strains comprise the strain having the deposit accession number NRRL B-50017.

9. A method for preventing and/or reducing planktonic proliferation of microorganisms, comprising subjecting the microorganism(s) in an aqueous solution to one or more bacterial strains, wherein the one or more bacterial strains comprise:
the strain having the deposit accession number NRRL B-50017;
the strain having the deposit accession number PTA-7541;
the strain having the deposit accession number PTA-7542;
the strain having the deposit accession number PTA-7543;
the strain having the deposit accession number PTA-7545;
the strain having the deposit accession number PTA-7546;
the strain having the deposit accession number PTA-7791; or
a mixture of two or more of the strains.

10. The method of claim 9, wherein planktonic proliferation is caused by *Pseudomonas*.

11. The method of claim 9, wherein the method is repeated periodically.

12. The method of claim 9, wherein a dosage of the bacterial strains cell count is in the range from 1 to $1\times10^8$ cfu/mL.

13. The method of claim 9, wherein the one or more bacterial strains comprise the strain having the deposit accession number NRRL B-50017.

* * * * *